United States Patent [19]

Kuroda et al.

[11] 4,099,419
[45] Jul. 11, 1978

[54] ULTRASONIC TOMOGRAPHY APPARATUS

[75] Inventors: Masao Kuroda, Tokyo; Toshio Kondo, Kunitachi; Toshio Ogawa, Kokubunji; Sekijyuro Ono, Hachioji, all of Japan

[73] Assignee: Hitachi Medical Corporation, Japan

[21] Appl. No.: 773,171

[22] Filed: Mar. 1, 1977

[30] Foreign Application Priority Data

Mar. 5, 1976 [JP] Japan .................................. 51-23276

[51] Int. Cl.² ............................................ G01N 29/00
[52] U.S. Cl. ..................................... 73/626; 128/2 V
[58] Field of Search ................... 73/67.7, 67.85, 67.9, 73/625, 626; 128/2 V, 2.05 Z

[56] References Cited

U.S. PATENT DOCUMENTS

| | | | |
|---|---|---|---|
| 3,090,030 | 5/1963 | Schuck | 73/67.8 S X |
| 3,778,757 | 12/1973 | Houston | 73/67.7 |
| 3,789,833 | 2/1974 | Bom | 128/2.05 Z X |
| 3,881,466 | 5/1975 | Wilcox | 128/2 V |
| 3,919,683 | 11/1975 | Itamura et al. | 73/67.9 |
| 3,936,791 | 2/1976 | Kossoff | 73/67.8 S X |
| 3,983,374 | 9/1976 | Sorensen et al. | 73/67.8 S X |
| 4,019,169 | 4/1977 | Takamizawa | 73/67.8 S X |

*Primary Examiner*—Charles A. Ruehl
*Attorney, Agent, or Firm*—Craig & Antonelli

[57] ABSTRACT

There is disclosed an ultrasonic tomography apparatus of electronic scanning type in which an array of ultrasonic transducer elements are excited with desired time delays allotted for the transducer elements thereby to transmit and receive ultrasonic beams at a deflection angle corresponding to the desired time delays, and the received echo signal of the ultrasonic beams is displayed on a CRT display device in a form of a tomograph of a sample to which the ultrasonic beams are directed. The apparatus comprises a memory in which both of first signals representative of the time delays given to the transducer elements in dependence on given deflection angles and signals designating display position in the X- and Y-directions of the CRT are previously stored and read out for producing delays allotted for the transducer elements and displaying the received echo signal on the CRT.

7 Claims, 9 Drawing Figures

ULTRASONIC TOMOGRAPHY APPARATUS

FIELD OF THE INVENTION

This invention relates to an ultrasonic tomography apparatus for producing an ultrasonic tomograph in a display device such as a cathode-ray tube (hereinafter referred to as CRT) from an echo signal obtained by irradiating an object or sample to be examined such as the human body with ultrasonic beams. In particular, the invention concerns a tomograph display apparatus in which signals available from the scanning of a sample with the ultrasonic transducer under the control of electronic apparatus are utilized to display the tomograph of the sample.

DESCRIPTION OF THE PRIOR ART

Figure 1A:
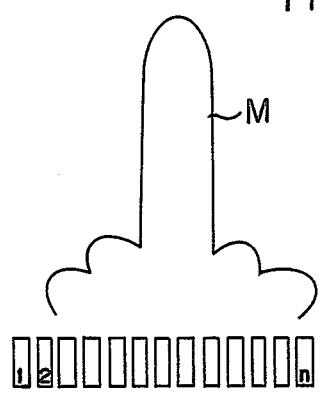
FIGS. 1a to 1c illustrate directivity characteristics of an ultrasonic transducer array.
Figure 1B:
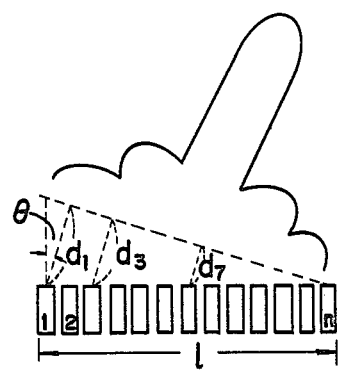
Figure 1C:
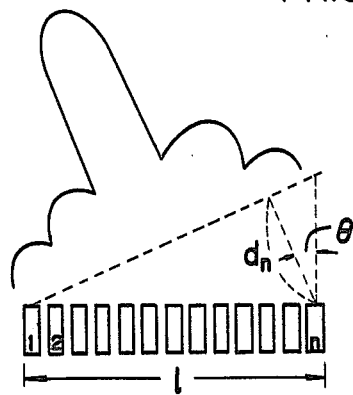

Heretofore, electronic deflection of the ultrasonic beams has been accomplished by means of an array of ultrasonic transducers wherein the individual transducers are excited at different time points, i.e. with a time delay with respect to one another thereby to deflect the ultrasonic beam. Such a prior art deflection method is illustrated in FIGS. 1a to 1c. When $n$ ultrasonic transducer elements 1 to $n$ arranged in a linear array are simultaneously excited, the primary or main beam M of the ultrasonic wave will extend orthogonally to the linear array of the transducers, as will be seen from FIG. 1a. On the other hand, when the individual transducer elements 1 to $n$ are excited with respective time delays $\tau_1$ to $\tau_n$ (wherein $\tau_1 = d_1/v, \ldots \tau_n = d_n/v$, $v$ being sound velocity in the medium to be examined and $\tau_1 > \tau_n$) so that the fronts of the sound waves emitted from the individual transducers are in phase with each other at locations spaced by distances $d_1, \ldots, d_n (d_1 > _n)$ from the individual transducer elements, then the main beam will be deflected for an angle $\theta$ ($\theta = \sin^{-1} v\tau_n/l$ where $l$ represents the length of the transducer array), as is shown in FIG. 1b. In a similar manner, the main beam can be deflected for an angle $-\theta$ under the conditions that $d_1 < d_n$ or $\tau_1 < \tau_n$, as can be seen from FIG. 1c.

Figure 2:
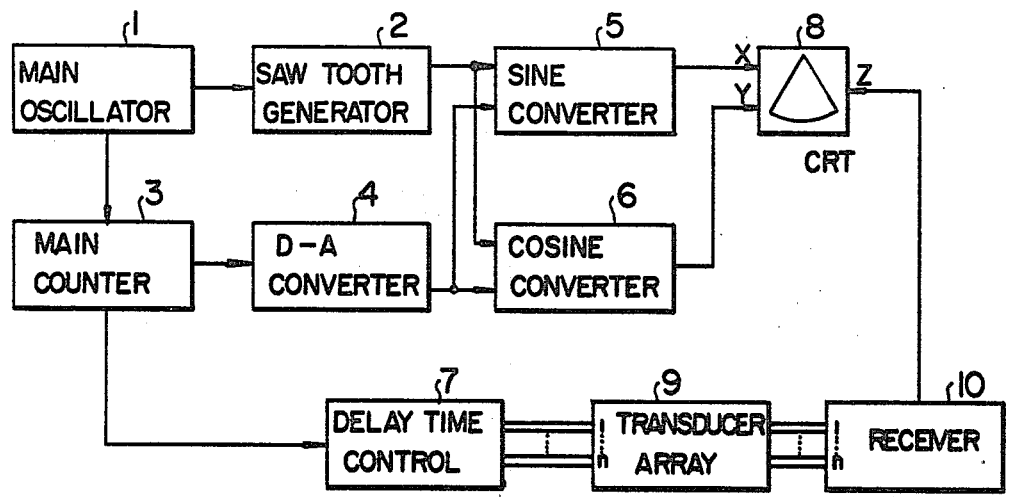
FIG. 2 is a block diagram showing an arrangement of hitherto known ultrasonic wave tomography apparatus.

As will be appreciated from the above description, it is possible to deflect the main beam of an ultrasonic wave by exciting the individual transducer elements in the array with appropriate time delays. It is also possible to perform the scanning with the ultrasonic main beam in a sector-like pattern on the basis of the same principle as the beam deflection. In this connection, it will be appreciated that, when the echo of the ultrasonic beam is to be displayed on a CRT with brightness modulation after the received echo has been matched in phase with a view to allowing the visual observation, the electron beam of the CRT has to be deflected in a sector-like scanning pattern in synchronism with the excitation timing of the transducer array. To this end, there has been proposed a circuit arrangement shown in FIG. 2. Referring to the figure, an output signal from a main oscillator 1 is supplied to a main counter 3 and a sawtooth generator 2. The instantaneous contents of the main counter 3 are converted into an analog signal through a D-A converter 4 and applied to one input of a sine converter 5 and a cosine converter 6. The sawtooth generator 2 is triggered by the signal from the main oscillator 1 to produce a sawtooth wave signal at the output thereof. The output signal from the sawtooth generator is applied to the other inputs of the sine converter 5 and the cosine converter 6, which function, respectively, to multiply the output signal from the D-A converter 4 with factors "sine" and "cosine". The output signals from the sine and the cosine converters 5 and 6 are applied, respectively, to X- and Y-deflecting systems of CRT 8.

The main counter 3 serves to control a delay time control circuit 7 so that delay times are given to individual elements of an ultrasonic transducer array in dependence on the outputs from the main counter 3. Thus, the transducer elements 1 to $n$ such as shown in FIG. 1a are excited with respectively allotted delay times in synchronism with the timing of the main oscillator 1. A receiver means 10 is provided to receive the echo of the ultrasonic wave emitted from the transducer array 9 and produce brightness signal for CRT 8. The receiver means 10 of course incorporates therein a means for performing the phase-matching of the received signals from the individual transducer elements.

With the above-described arrangement, the ultrasonic beam as well as the scanning electron beam of the CRT can be deflected in a sector-like pattern. The echo of the ultrasonic beam is displayed on the CRT with brightness modulation, allowing the visual observation of the tomograph of the object to be examined. In general, the transducer array 9 is employed also as a receiver constituting the receiver means 10.

The hitherto known apparatus of the arrangement described above has however the following drawbacks. In general, the scanning in the sector-like pattern is effected by deflecting successively the ultrasonic beam from one end to the other of the sector with the ultrasonic beam having directivity in the deflected direction upon emission as well as reception thereof. However, the directivity is not usually sharp, i.e. the beam has an appreciable lateral extension or width. Accordingly, when the emission angle is to be varied for a succeeding deflection of the ultrasonic beam in the scanning, a time delay several times as long as the display or observing time duration is required in order to be immune to the influences of echoes produced in the preceding scanning deflections. As a result, it is impossible to have a short time interval between the successively effected deflections of the emitted ultrasonic beam from the transducer array. In this manner, the successively scanning method in which the ultrasonic beam is sequentially deflected from one end to the other of the sector pattern requires a lot of time for obtaining a desired tomograph. Reduction in the time duration for obtaining a tomograph may be accomplished by emitting the succeeding ultrasonic beam in the direction which does not fall within the width of directivity of the preceding ultrasonic beam, i.e. in the direction outside of the side lobe or corresponding to the zero directivity of the preceding beam after the observation relative thereto has been made. However, it is impossible to produce the raster lines of sector in any arbitrary sequence with the arrangement shown in FIG. 2 or, otherwise, specific function generators would be required in place of the sine and cosine converters 5 and 6, which involves complexity in the circuit arrangement inclusive of the delay time control circuit 7 which is adapted to produce delay times for each of the transducer element of the array 9.

SUMMARY OF THE INVENTION

An object of the invention is therefore to provide an ultrasonic wave tomography apparatus having decreased emission time of the ultrasonic wave.

Another object of the invention is to provide an ultrasonic wave tomography apparatus in which the deflecting range of the ultrasonic beam can be selected in a desired manner.

With the above objects in view, the invention contemplates to store previously in a storage means the delay times allotted for the individual transducer elements to produce corresponding deflection angles and signal indicating locations of the ultrasonic beam on a display device.

DESCRIPTION OF THE PREFERRED EMBODIMENTS

Figure 3:
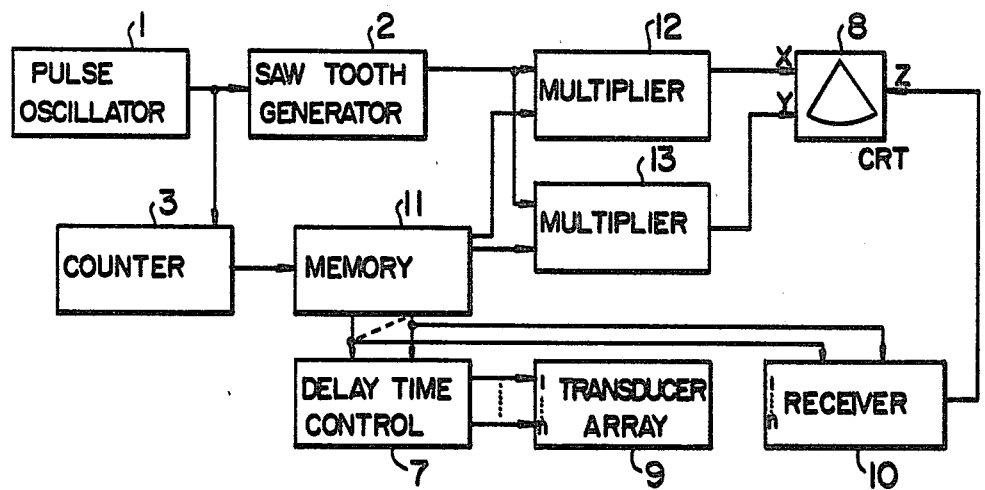
FIG. 3 is a block diagram showing an arrangement of the ultrasonic wave tomography apparatus according to an embodiment of the invention.
Figure 4:
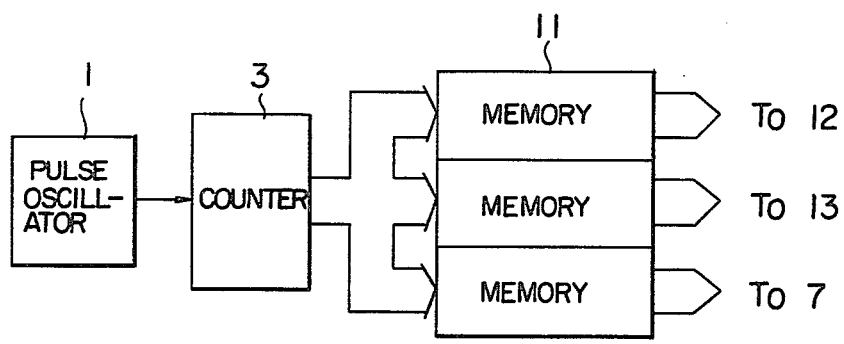
FIGS. 4 and 5 schematically show main portions of the same.

Referring to FIG. 3 which shows an ultrasonic wave tomography apparatus according to an embodiment of the invention, reference numeral 11 denotes a storage device or memory which previously stores therein in a form of sets of data the display position command signals for controlling a display means such as the CRT in correspondence with angles formed by raster lines constituting a sector pattern in accordance with the scanning sequence and the delay quantities (delay times) given to the individual transducer elements. It will of course be appreciated that the delay quantities themselves need not be stored but signals representative thereof may be placed in the storage means or memory 11. As is shown in FIG. 4, the memory 11 can be accessed by a data access means constituted by a pulse oscillator 1 and a counter 3 so that the signals for commanding the display positions of the sine, cosine and like values in accordance with the output from the counter 3 and the signals representative of the delay times can be read out in parallel and input to multipliers 12, 13 and a delay time control circuit 7. In this connection, it will be understood that both of these signals may be serially read out and stored in another memory device. With such an arrangement, it is possible to determine arbitrarily the sequence of selecting the deflection angles in dependence on the manner in which the data are stored in the memory 11. In the illustrated embodiment, the sine values stored in the memory 11 are fed to the multiplier 12 with the cosine values applied to the multiplier 13 to be multiplied by the signal generated by a sawtooth generator 2. The output signals from the multipliers 12 and 13 are supplied, respectively, to the X- and Y-deflecting systems of the CRT 8. On the other hand, the individual transducer elements 1 to $n$ of the transducer array 9 are excited with respectively allotted delay times in dependence on the output signals from the delay time control circuit 7 to which the signals representative of the delay times are applied for the memory 11. The apparatus of the above-described arrangement is evaded from the disadvantages of the hitherto known apparatus. In other words, the sequence or order of producing a sector can be selectively changed by correspondingly varying the stored positions or relations of data in the memory 11.

Figure 5:
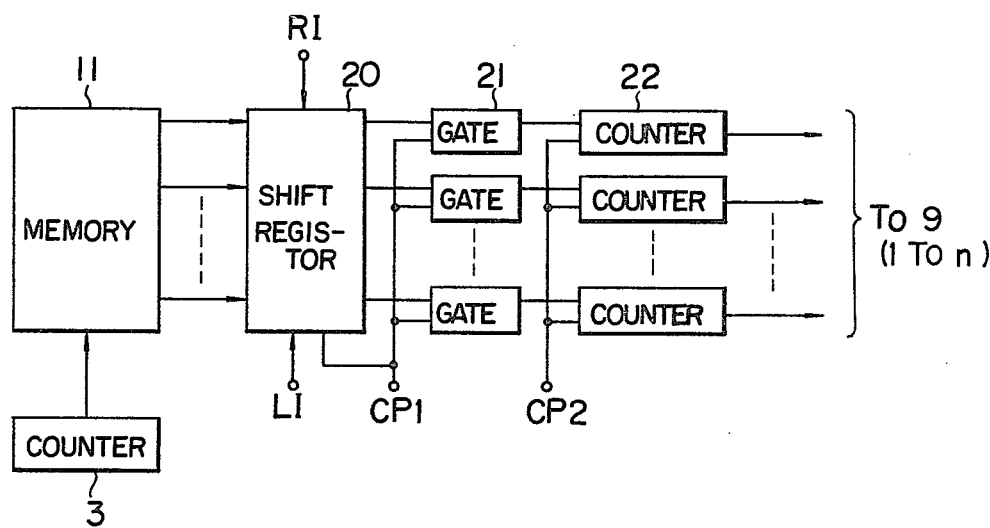

Next, description will be made on the delay quantity and a method for controlling the application of the delays to the individual transducer elements. Referring to FIG. 5 which illustrates an arrangement for driving the delay time control circuit 7 and the transducer array 9 in dependence on the contents stored in the memory 11 in accordance with the teaching of the invention, the counter 3 serves to sequentially count the pulses from the oscillator 1. In response to each counting, the corresponding memory addresses in the memory 11 are selected and the signals $M_{\theta(i)}$ (where $i$ represents natural number of $l$ to $n$ which represents the total number of the transducer elements of the array 9) for determining time delays corresponding to the deflection angles predetermined for each of the individual transducer elements of the array 9 are read out in parallel. The signals $M_{\theta(i)}$ are previously selected for all the deflection angles $\theta$ and stored in the memory. The signal $M_{\theta(i)}$ represents the quantity which is determined depending on whether a value obtained by quantizing the required delay time by a certain value becomes different between the adjacent transducer elements.

More particularly, assuming that the number of the transducer elements is represented by N, the total delay time $\tau$ is divided by the number $(N - 1)$ of gaps between the arrayed transducer elements. The resultant quotient is then quantized by a delay time $\tau_o$. The quantized delay time $\tau_i$ is thus given by the following expression:

$$\tau_i = [(\tau \cdot i)/(N - 1)/\tau_o] \quad (i = 0, 1, 2, \ldots, N - 1)$$

Here, $\tau$ is equal to $l/v \sin \theta$. $\theta$ is deflection angle, $l$ is length of the array and $v$ is sound velocity. Subsequently, differences between the quantized delay times for the adjacent transducer elements, i.e. $\tau_{i+1} - \tau_i$ ($i = 0, 1, 2, \ldots, N - 1$) are determined and the delay times corresponding to these difference values are given to the ultrasonic emissions. In this connection, the range of the deflection angles of the ultrasonic beams is determined as the range of angle in which the difference values between the quantized delay times for the adjacent transducer elements take "1" and "0". More particularly, the difference value represented by $M_{\theta(i)}$ can be calculated in the following manner. Assuming that the initial value of $n$ (positive interger) is "1" and that $M_{\theta(i)}$ ($i = 1, 2, \ldots, N$) takes a value equal to "1" or "0", values of $i$ which satisfies the following relation are determined with $i$ being varied from $l$ to $N$.

$$(\tau_\theta/\tau_o i - n) > 0$$

Every time the above relation is satisfied, definition is made such that $M_{\theta(i)} = $ "1". By increasing the value of $n$ for one increment, the values of $i$ which satisfy the above relation are sequentially determined. In this manner, a series of values of $M_{\theta(i)}$ which are equal to "1" or "0" are calculated for the deflection angles $\theta$ for the sector scanning under the condition that $\tau_\theta < \tau_o$.

For example, assuming that the number N of transducers is 32, the gap $\Delta$ between the transducer elements is 0.5 mm, the velocity of sound in the medium to be examined is 1500 m/sec and the quantizing value is 50 $n$ sec, then value of $M_{\theta(i)}$ for $\theta = 0$ (zero) and $i = 1$ to 32 will be binary 0, 0, 0, 0, 0, 0, 0, 0, 0, 0, 0, 0, 0, 0, 0, 0, 0, 0, 0, 0, 0, 0, 0, 0, 0, 0, 0, 0 and 0. In the case of $\theta$ = 4.3° and $i$ = 1 to 32, $M_{\theta(i)}$ will take binary values of 0, 0, 1, 0, 1, 0, 1, 0, 1, 0, 1, 0, 1, 0, 1, 0, 1, 0, 1, 0, 1, 0, 1, 0, 1, 0, 1 and 0. In the case of $\theta$ = 8.6° and $i$ = 1 to 32, values of $M_{\theta(i)}$ will then take 0, 1, 1, 1, 1, 1, 1, 1, 1, 1, 1, 1, 1, 1, 1, 1, 1, 1, 1, 1, 1, 1, 1, 1, 1, 1, 1, 1, 1, 1 and 1.

The values of $M_{\theta(i)}$ determined for all the detection angles $\theta$ which satisfy the condition that $\tau_\theta < \tau_0$ are utilized for controlling the delay times allotted for the individual transducer elements.

In FIG. 5, reference numeral 11 denotes a memory, reference numeral 20 designates a bidirectional shift register of $n$ bits, symbol $R_1$ designates a serial input terminal of the shift register 20, symbol $L_1$ designates another serial input terminal, numeral 21 designates gates each having one input coupled to each of the outputs of the shift register 20, numeral 22 designates up-down counters each having one input coupled to each of the outputs of the gates 21, numerals $l$ to $n$ designate transducer elements of the array 9 to which the outputs of the counter 10 are respectively applied, symbol $CP_1$ designates a clock or timing signal input terminal, and symbol $CP_2$ designates a pulse input terminal.

Under the condition that $\tau_\theta < \tau_0$, the values of $M_{\theta(i)}$ described above are stored in the memory 11. When desired deflection angles $\theta$ are to be generated, the addresses of the memory corresponding to the desired values of $\theta$ are accessed whereby desired values of $M_{\theta(i)}$ are selectively read out. The values $M_{\theta(i)}$ read out from the memory are applied to a preset input terminal of the presettable shift register 20 of $n$ bits. Outputs from the shift register 20 are applied to one input of the gates 9 which are enabled to pass therethrough clock pulses to the associated up-down counters.

The clock pulses $P_1$ applied to the clock pulse input terminals of the counters 22 are the same as the shift pulses for the shift register 8. In the initial state, the serial input of the shift register 20 is set to "0" through the serial input terminal RI. In FIG. 5, although the clear terminal is omitted from illustration, contents of all the counters 22 are reset to "0's " through the clear terminal in the initial state and desired values of $M_{74(i)}$ stored in the memory are preset in the shift register 20.

When $m$ clock pulses $P_1$ equal in number to the transducer elements are supplied to the counters 22 in the initial state described above, the contents of each counter at the time of j-th clock pulse are given by the expression $$CT_j = \sum_{i=1}^{j} M_{\theta(i)}.$$

This means that the contents of the counters 22 are quantized by $\tau_o$ in the proportionally divided states of $CT_L$ to $CT_m$.

After the proportionally divided weights have been placed in the counters 22, subtraction (or addition) pulses $P_2$ are applied to the counters through the terminal $CP_2$ upon excitation of the transducer elements, and the borrow or carry pulses of the individual counters are employed as the exciting pulses for the associated transducer elements. In this manner, the main beam of the ultrasonic waves generated by the transducer element can be deflected with desired deflection angles $\theta$.

Under the condition that $\tau_\theta \geq \tau_0$, application of $m$ clock pulses to the shift register 20 in the backward direction is repeated with the serial input signals applied thereto through the terminal LI being set to binary "1" for a number of times corresponding to the integer number of the ratio $\tau_\theta/\tau_0$. The maximum bit number of the up-down counter 22 is set to $(\tau_{\theta max}/\tau_0) \times m$.

In the above description, it has been assumed that the deflection is effected in the positive direction of $\theta$. In the case of the deflection to be effected in the opposite direction corresponding to $-\theta$, this can be accomplished merely by reversing the shifting direction of the shift register 20 shown in FIG. 5.

The receiver means 10 is supplied with the output signals $M_{\theta(i)}$ which are utilized to effect the phase matching thereby to produce the brightness modulating signal for the CRT. In this connection, it will be appreciated that the signals $M_{\theta(i)}$ will serve as delay time selecting signals for delay elements (tap selecting signals for LC-delay elements, for example) interposed between the outputs of the transducer elements of a so-called differential type ultrasonic wave receiving system.

According to the teaching of the invention, the arrangement of the delay time control circuit 7 can be simplified.

The delay time $\tau_\theta$ given to the transducer elements for a given deflection angle can be expressed by $l \cdot \sin\theta/V$. In the range where values of $\theta$ remain small, $\tau_\theta$ is approximately equal to $l \cdot \theta/v$. When equal increments are made in variation of $\tau_\theta$ in the above range, the deflection angle of the CRT will vary in nearly equal increments. However, when $\theta$ becomes greater, the above approximation will be invalid and the correspondence between the emitted direction of the ultrasonic beam and the bright line on the CRT may be no more recognized. It is thus necessary that either the deflection angle or $\tau_\theta$ should have a non-linear factor. However, according to the teaching of the invention, data stored in the memory 11 can be so composed that the correspondence between the emitted direction of the ultrasonic beam and the bright line on the CRT may be constantly maintained regardless of whether the deflection is effected with equal increments of the deflection angle or with equal increments of $T_\theta$, which in turn allows the arrangement of the apparatus to be implemented in a simplified configuration.

Figure 6:
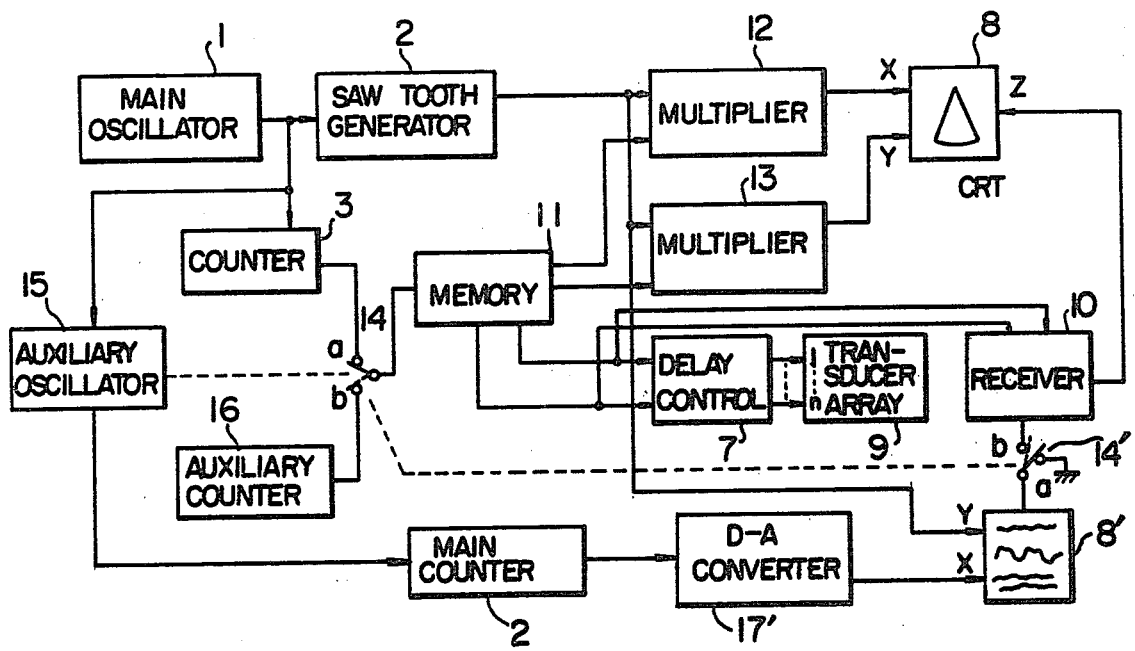
FIG. 6 is a block diagram showing another embodiment of the invention.

FIG. 6 is a block diagram showing another embodiment of the invention which comprises an auxiliary oscillator having an oscillation frequency lower than that of the main oscillator 1 shown in FIG. 3. Main oscillation of the oscillator 1 is interrupted for a predetermined interval under the timing control of the auxiliary oscillator. During the interrupted period, selection of addresses of the memory is performed with the aid of the contents in an auxiliary counter set to a predetermined value, thereby to permit various displays if desired. (In the embodiment shown in FIG. 6, the counting function is unnecessary in essence. However, for the display of scanning M mode, the counting function is required, as described hereinafter. The auxiliary counter is employed to this end.)

In the description of the embodiment shown in FIG. 6, it is assumed that M mode ultrasonic cardiograph (UCG) in a given angular direction of the sector-like scanning pattern is to be obtained in addition to the tomograph described hereinbefore. In accordance with the M mode operation, the propagating direction of the ultrasonic beam emitted in a given direction is taken along the Y-axis of a display system with the elapsing time taken along the X-axis, while the brightness modulation in the display system is effected in dependence on the intensity of the received echo.

Referring to FIG. 6, reference numeral 15 denotes the auxiliary oscillator for generating a frequency lower than that of the main oscillator 1 in synchronism with the latter. The auxiliary oscillator 15 may be composed of a frequency divider for dividing the output frequency of the main oscillator 1 and has an output connected to the input of an additional main counter 2', the output of which in turn is coupled to a D-A converter 17 connected to the X-deflection system of an additional CRT 8'. The main counter 2' and the D-A converter 17 constitutes, so to speak, a kind of sawtooth generator. The scanning in the X-direction of the CRT 8' is thus effected at a lower rate.

The output signal from the sawtooth generator 2 is applied to the Y-deflection system of CRT 8' which has a Z signal (brightness signal) system adapted to be applied with output signal from the receiver means 10 through a change-over switch 14'. Reference numeral 16 denotes the auxiliary counter having an output connected to the input of the memory 11 through a change-over switch 14. The switches 14 and 14' are adapted to be changed over to the position b by a timing clock from the auxiliary oscillator 15 thereby to produce the waveform of M-mode on CRT 8'. Assuming that the frequency of the main oscillator 1 is 5 KHz while that of the auxiliary oscillator 15 is 500 Hz, the waveform of M-mode can be obtained in a ratio of 1 to 10 raster lines of the sector pattern. In this manner, the tomograph can be observed on a real time basis through the time division simultaneously with the waveform of M-mode in a given direction. (The raster line can be arbitrarily selected in accordance with the contents of the auxiliary counter 16.) In this case, the set direction can be displayed on CRT 8, because the scannings through the electron beam in this direction are effected more times than the scanning in the other direction, whereby a brightness of a higher intensity is produced in the set direction. As an alternative, blanking operation may be effected in the other direction. Further, since the sweeping operation is performed under the control of the counting function of the auxiliary counter 16, M-mode as scanned on the tomograph can be easily observed.

Figure 7:
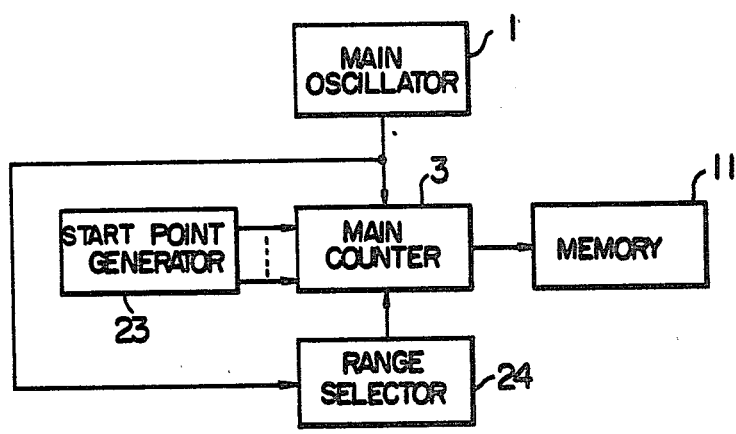
FIG. 7 shows in a block diagram still another embodiment of the invention.

FIG. 7 shows another embodiment of the invention according to which a narrow range selecting means is provided in the data accessing means shown in FIG. 3.

As will be appreciated from the foregoing description, the maximum angular range (hereinafter referred to as wide range) of the beam deflection in the sector-like scanning pattern is determined by the data stored in the memory 11. (Of course, resolution power and the like factor are considered in the storage of data.) It would be highly desirable if a narrow range constituting a given part of the wide range could be selectively displayed. For example, in the case where a moving organ of the human body such as the heart or cordia is observed, it is very advantageous the wide range is first employed and subsequently only a region of interest is observed in the narrow range, thereby to decrease the time duration required for producing the image to be observed and allow the observation only of a portion of a moving organ such as valve membrane of the heart on the approximated real time basis. To this end, the embodiment shown in FIG. 7 has a means for repeatedly displaying a narrow range selected from the wide range set in the memory 11. Referring to the figure, numeral 24 denotes a range selector driven by the main oscillator 1, which selector serves to preset the state of a start point generator 23 in the main counter 3. In this case, the counter 3 is composed of a presettable counter. The range selector 24 produces a timing signal for several raster lines of the sector-like pattern and may be composed of a counter.

With the above arrangement in which the range selector 24 functions to restrict the range width and the start point generator 23 serves to vary arbitrarily the scanning start position, it is possible to select out a desired narrow deflection range. By way of example, the start point generator 23 is so arranged that a binary code which represents an address of the memory corresponding to a given deflection angle and can be optionally selected.

The apparatus according to the invention described in the foregoing do not require non-linear elements for the sine, cosine or the like conversion and can be so modified as to produce deflection patterns other than the sector-like shape. Further, the control apparatus can be implemented in a simplified arrangement, and the time required for emission of the ultrasonic beam can be significantly reduced. Besides, the apparatus can be easily so modified that M-mode of a give angular direction can be displayed simultaneously with the tomograph and/or a desired narrow range can be selectively taken out from the wide deflection range.

We claim:

1. In an ultrasonic tomography apparatus of an electronic scanning type in which an array of ultrasonic transducer elements are excited with desired time delays allotted for the individual transducer elements thereby to transmit and receive ultrasonic beams at a deflection angle corresponding to said time delays, the received echo signal of said ultrasonic beams being displayed on a display means in a form of a tomograph of a sample to which said ultrasonic beams are directed, the improvement comprising a memory means for previously storing therein first signals representing the time delays selectively allotted for said individual transducer elements in dependence on given deflection angles and second signals commanding display position on said display means, and a data accessing means for reading out said first and second signals corresponding to a desired deflection angle from said memory means, said signals read out through said data accessing means being utilized to provide said time delays for said transducer elements upon excitation thereof and to display said received echo signal on said display means.

2. An apparatus as set forth in claim 1, wherein said data accessing means includes a main oscillator and a main counter for counting the oscillation frequency of said main oscillator.

3. An apparatus as set forth in claim 2, further comprising a second display means and wherein said data accessing means further includes an auxiliary oscillator having an oscillation frequency lower than that of said main oscillator and adapted to be operated in synchronism with said main oscillator, the data reading-out operation through said main counter being interrupted upon appearance of output signal from said auxiliary oscillator, and means for selecting address of said memory means corresponding to a predetermined deflection angle, the received echo signal obtained through the delay signal at said selected address being displayed on said second display means.

4. An apparatus as set forth in claim 1, wherein sine and cosine values are used as the display position commanding signals stored in said memory means.

5. An apparatus as set forth in claim 4, further comprising multipliers for multiplying said sine and cosine values read out from said memory means with a sawtooth wave signal, the outputs of said multipliers being coupled to X- and Y-deflecting systems of said display means.

6. An apparatus as set forth in claim 1, wherein said data accessing means includes narrow range selecting means.

7. An apparatus as set forth in claim 6, wherein said data accessing means provided with said narrow range selecting means includes a main oscillator, a presetable main counter for counting the output of said main oscillator, a start point generator connected to a preset input of said main counter and adapted to produce a signal for designating address of said memory at which data relative to the point for starting the scanning of said narrow range are stored, and a range selector having an input coupled to the output of said main oscillator and adapted to generate a signal for presetting said addressing signal for said start point generator in said main counter.

* * * * *